United States Patent
Wei

(10) Patent No.: US 8,622,961 B2
(45) Date of Patent: Jan. 7, 2014

(54) SAFETY NEEDLE ASSEMBLY WITH DISPLACEABLE LOCKING TONGUE

(75) Inventor: Min Wei, Morris Plains, NJ (US)

(73) Assignee: Becton, Dickinson & Company, Franklin Lakes, NJ (US)

(*) Notice: Subject to any disclaimer, the term of this patent is extended or adjusted under 35 U.S.C. 154(b) by 0 days.

(21) Appl. No.: 13/517,491

(22) PCT Filed: Dec. 22, 2009

(86) PCT No.: PCT/US2009/069182
§ 371 (c)(1),
(2), (4) Date: Jun. 20, 2012

(87) PCT Pub. No.: WO2011/078851
PCT Pub. Date: Jun. 30, 2011

(65) Prior Publication Data
US 2012/0259281 A1    Oct. 11, 2012

(51) Int. Cl.
*A61M 5/00* (2006.01)
*A61M 5/32* (2006.01)

(52) U.S. Cl.
USPC .......................... 604/110; 604/263; 604/195

(58) Field of Classification Search
USPC .................. 604/111, 263, 97.02, 89–91, 162, 604/195–196, 198, 192, 165.01, 187
See application file for complete search history.

(56) References Cited

U.S. PATENT DOCUMENTS

| | | | |
|---|---|---|---|
| 4,795,432 A | 1/1989 | Karczmer | |
| 4,994,045 A | 2/1991 | Ranford | |
| 5,312,370 A | 5/1994 | Talonn et al. | |
| 6,986,760 B2 | 1/2006 | Giambattista et al. | |
| 7,905,866 B2 | 3/2011 | Haider et al. | |
| 8,177,745 B2* | 5/2012 | Brechbuehler et al. | 604/110 |
| 2001/0039387 A1* | 11/2001 | Rutynowski et al. | 600/573 |
| 2003/0139705 A1 | 7/2003 | Larsen et al. | |
| 2004/0122379 A1 | 6/2004 | Bosse et al. | |
| 2005/0038392 A1 | 2/2005 | DeSalvo | |
| 2005/0159709 A1 | 7/2005 | Wilkinson | |
| 2009/0088696 A1 | 4/2009 | Harding et al. | |
| 2011/0022001 A1* | 1/2011 | Wei | 604/198 |
| 2011/0288526 A1* | 11/2011 | Wei | 604/506 |
| 2012/0109052 A1* | 5/2012 | Wei et al. | 604/82 |
| 2012/0277724 A1* | 11/2012 | Larsen et al. | 604/506 |

FOREIGN PATENT DOCUMENTS

| | | |
|---|---|---|
| WO | 9117783 | 11/1991 |
| WO | 2004014458 A2 | 2/2004 |
| WO | 2005079441 A2 | 9/2005 |
| WO | 2007142746 A1 | 12/2007 |

* cited by examiner

*Primary Examiner* — Nicholas Lucchesi
*Assistant Examiner* — Rebecca E Eisenberg
(74) *Attorney, Agent, or Firm* — Hoffmann & Baron, LLP

(57) ABSTRACT

A safety needle assembly is provided herein which includes a displaceable locking tongue which has a first position in which the locking tongue covers an aperture formed in a shield so as to prevent the passage therethrough of a needle. A biasing element is also provided for urging the locking tongue to the first position. The locking tongue is releasably retained in a retained position prior to use of the safety needle assembly, the aperture being sufficiently uncovered with the locking tongue being in the retained position so as to permit passage of the needle through the aperture. The locking tongue is releasably retained in the retained position against biasing force of the biasing element. With the shield being displaced proximally from a first position to a second position, the locking tongue is released from the retained position and permitted to be displaced to the first position under force of the biasing element. Advantageously, with the subject invention, a safety needle assembly is provided which covers a used needle after use and, optionally, provides a use indicator.

9 Claims, 26 Drawing Sheets

SAFETY NEEDLE ASSEMBLY WITH DISPLACEABLE LOCKING TONGUE

FIELD OF THE INVENTION

This invention relates to safety needle assemblies and, more particularly, to safety needle assemblies having a displaceable locking element for restricting access to a used needle.

BACKGROUND OF THE INVENTION

Safety needle assemblies are known in the prior art. With many of these assemblies, a shield is provided which covers a needle so as to restrict access thereto. However, the shield may have an open end through which access may still be obtained to a used needle, even with the shield in a protective state.

In addition, many safety needle assemblies seek to continuously shield a needle before, during and after use. Thus, the shield is provided in a covered, shielded position both before and after use. It may be difficult to discern if a needle assembly has been used considering that the safety needle assembly looks the same before and after use.

SUMMARY OF THE INVENTION

In an aspect of the subject invention, a safety needle assembly is provided herein including a hub; a needle fixed to the hub, the needle having a distal end, formed for insertion into a patient, and a proximal end; and, a shield having a tubular body with a proximal end and a distal end, an aperture being formed in the distal end to allow passage therethrough of the distal end of the needle. The shield is axially displaceable proximally relative to the hub between a first position to a second position, where the needle extends through the aperture and the distal end of the needle is exposed. The assembly further includes a displaceable locking tongue which has a first position in which the aperture is sufficiently covered so as to prevent passage therethrough of the distal end of the needle. A biasing element is also provided for urging the locking tongue to the first position. The locking tongue is releasably retained in a retained position prior to use of the safety needle assembly, the aperture being sufficiently uncovered with the locking tongue being in the retained position so as to permit passage of the distal end of the needle through the aperture. The locking tongue is retained in the retained position against biasing force of the biasing element. With the shield being displaced from the first position to the second position, the locking tongue is released from the retained position and urged towards the first position under force of the biasing element. Advantageously, with the subject invention, a safety needle assembly is provided which covers a used needle after use and, optionally, provides a use indicator.

Optionally or alternatively, in a further aspect of the subject invention, a locking tongue may be provided for the proximal end of the needle.

As used herein, the term "proximal", and derivatives thereof, refer to a direction away from a patient during use. The term "distal", and derivatives thereof, refer to a direction towards a patient during use.

These and other features of the invention will be better understood through a study of the following detailed description and accompanying drawings.

BRIEF DESCRIPTION OF THE DRAWINGS

FIGS. 6-8 show schematically operation of a safety needle assembly formed in accordance with the subject invention with; FIG. 6 showing an initial, pre-use state, FIG. 7 showing a during-use state, and, FIG. 8 showing an after-use state;

FIGS. 17-19 show schematically operation of a second embodiment of a safety needle assembly formed in accordance with the subject invention, with; FIG. 17 showing an initial, pre-use state, FIG. 18 showing a during-use state, and, FIG. 19 showing an after-use state;

DETAILED DESCRIPTION OF THE INVENTION

Figure 1:
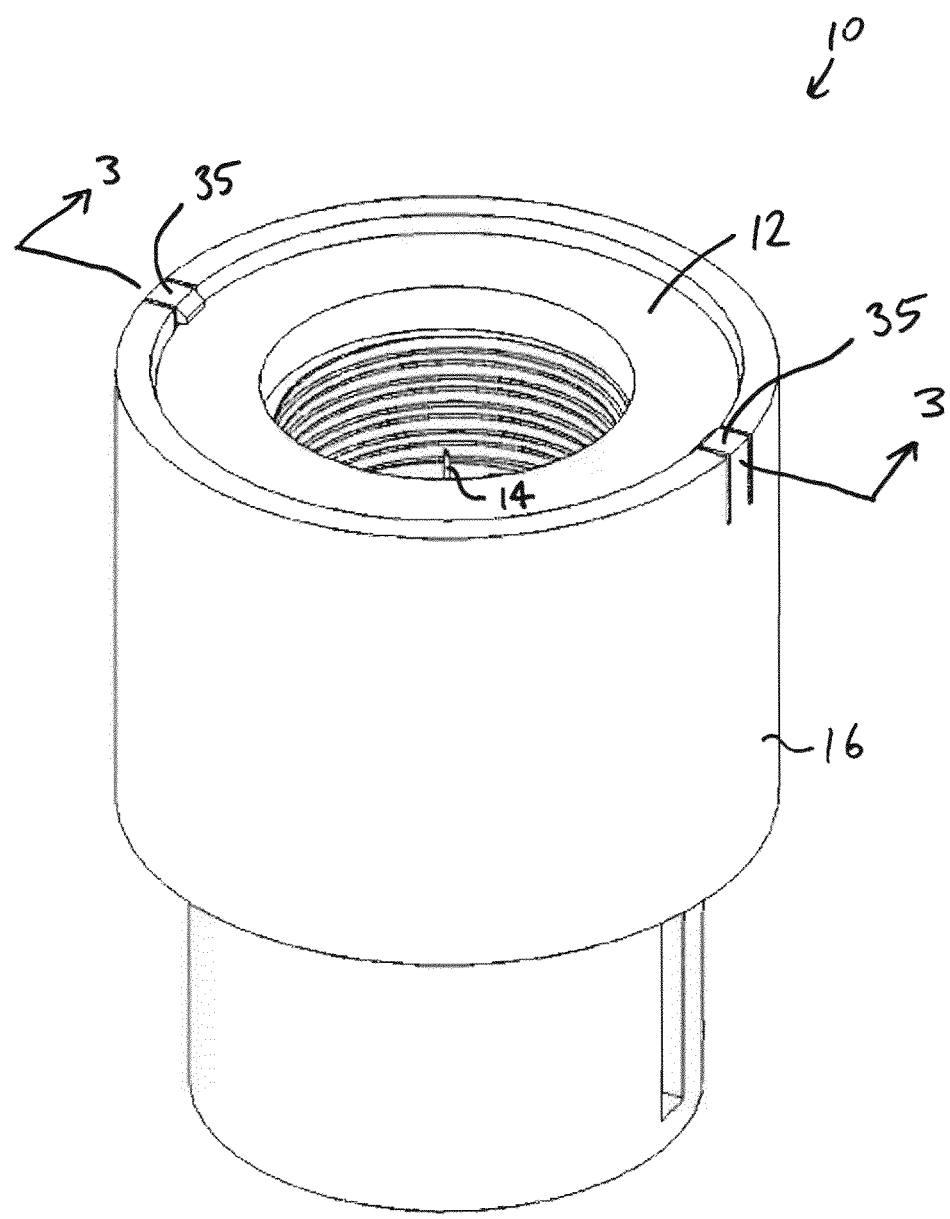
FIG. 1 is a perspective view of a safety needle assembly formed in accordance with the subject invention.
Figure 2:
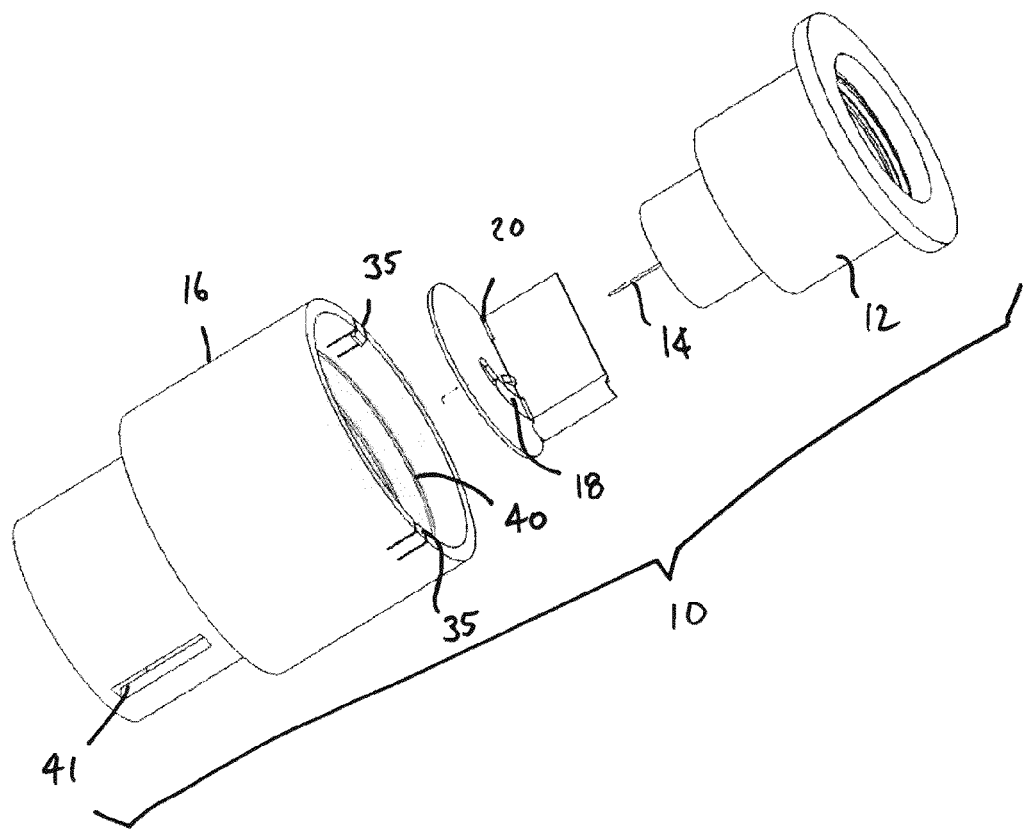
FIG. 2 is an exploded view of a safety needle assembly formed in accordance with the subject invention.

With reference to FIGS. 1-11, a first embodiment of a safety needle assembly is shown and generally designated with the reference numeral 10. The safety needle assembly 10 generally includes a hub 12, a needle 14, a shield 16, a displaceable locking tongue 18, and a biasing element 20 configured to apply force to the locking tongue 18 as described below. The safety needle assembly 10 may be used with various medical injectors, and is particularly well-suited for use with pen injectors.

Figure 3:
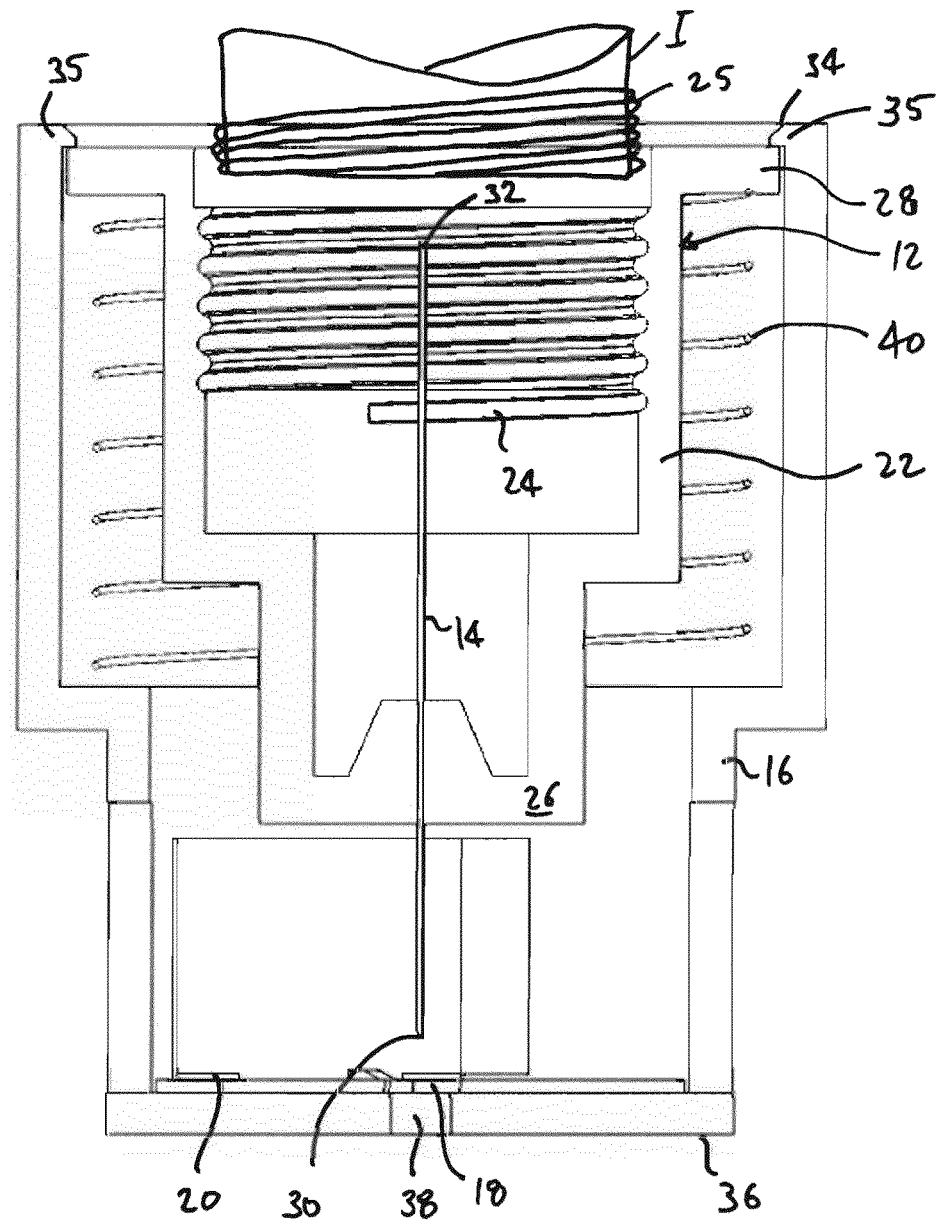
FIG. 3 is a cross-sectional view taken along line 3-3 of FIG. 1.

The hub 12, as best shown in FIG. 3, includes a tubular injector receiving portion 22 having mounting elements 24, such as threads, disposed therein formed to cooperatively engage corresponding mounting elements 25 on an injector I. The mounting elements 24 may, in addition, or alternatively, include tapered wall portions configured to provide a Luer mount onto an injector I. The hub 12 also includes a crosspiece 26 to which the needle 14 may be affixed in any known manner. A shoulder 28 is also provided to extend, continuously or discontinuously, radially outwardly from the hub 12.

The needle 14 includes a distal end 30, formed for insertion into a patient, and a proximal end 32. The needle 14 is positioned relative to the hub 12 such that the distal end 30 is located distally of the hub 12 and the proximal end 32 is located to be inserted into the injector I with the injector I being mounted to the hub 12. The needle 14 is provided with sufficient length to have the proximal end 32 extend into a reservoir contained in the injector I having contained therein drug or other agent intended for injection by the safety needle assembly 10.

The shield 16 is located about the hub 12 and includes a proximal end 34 and a distal end 36. An aperture 38 is formed in the distal end 36 to allow passage therethrough of the distal end 30 of the needle 14. The aperture 38 is formed larger than the needle 14 to ensure sufficient clearance therefor. The shield 16 is axially displaceable proximally relative to the hub 12 between a first position to a second position, where the needle 14 extends through the aperture 38 and the distal end 30 of the needle 14 is exposed (shown schematically in FIG. 7). Preferably, as shown in FIG. 3, in the first position, the distal end 36 of the shield 16 is located distally of the distal end 30 of the needle 14. Alternatively, as will be appreciated by those skilled in the art, the distal end 30 of the needle 14 may be initially located to extend from the aperture 38 to permit visual observation during priming of the needle 14 for use (i.e., the distal end 30 of the needle 14 may extend distally from the distal end 36 of the shield 16). The distal end 30 may only extend slightly. With this arrangement, the shield 16 is displaced proximally to the second position to operate in the same manner as the preferred embodiment.

Preferably, the safety needle assembly 10 includes a secondary biasing element 40 disposed to urge the hub 12 relative to the shield 16 to the shielding position shown in FIG. 3. The secondary biasing element 40 is preferably disposed about the hub 12 so as to act against the shoulder 28. The secondary biasing element 40 may be positioned against any portion of the shield 16, including a ledge 42 which may be located at the distal end 36 or along a mid-location of the shield 16 between the proximal end 34 and the distal end 36. One or more detents 35 may be formed on the shield 16 positioned to limit proximal movement of the hub 12 under force of the secondary biasing element 40.

Preferably, the locking tongue 18 is located within the shield 16 at or in proximity to the distal end 36. The locking tongue 18 is displaceable between a position, as shown in FIG. 4, in which the aperture 38 is sufficiently uncovered to permit passage therethrough of the distal end 30 of the needle 14, to a covered position, as shown in FIG. 5, where the locking tongue 18 sufficiently covers the aperture 38 so as to prevent passage therethrough of the distal end 30 of the needle 14.

Figure 4:
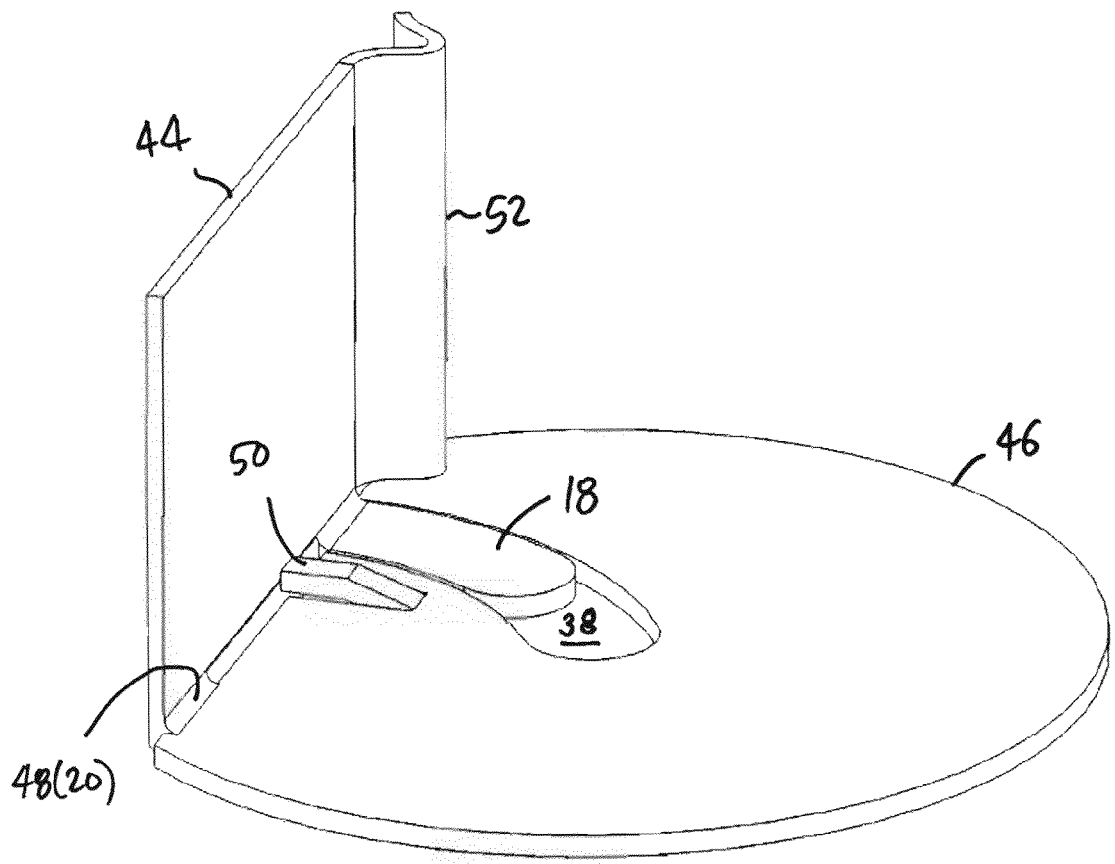
FIG. 4 is a perspective view of a locking tongue formed in accordance with the subject invention being in a retained position.
Figure 5:
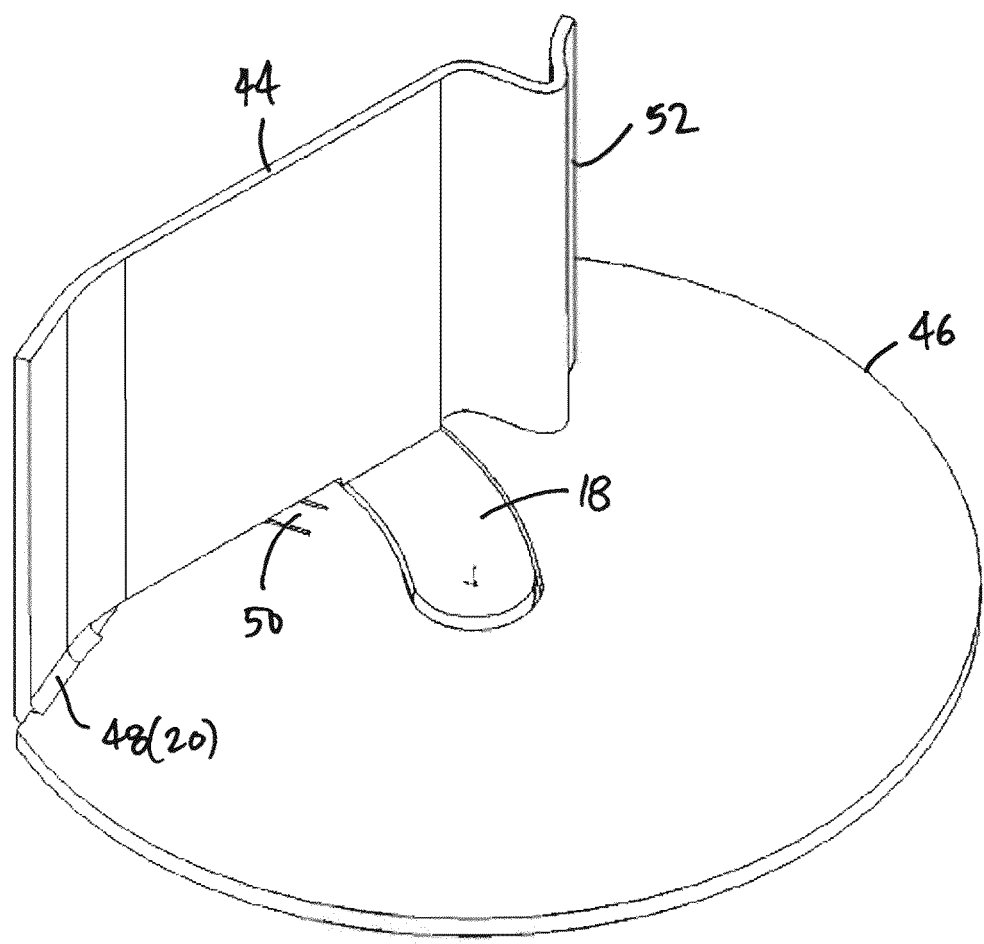
FIG. 5 is a perspective view of a locking tongue formed in accordance with the subject invention being in a covering position.

The biasing element 20 is configured to provide biasing force for urging the locking tongue 18 from the state shown in FIG. 4 to the state shown in FIG. 5. As will be appreciated by those skilled in the art, the biasing element 20 may be formed of various configurations. With reference to FIGS. 4 and 5, the biasing element 20 may include a swivable locking member 44 to which the locking tongue 18 is fixed so as to move in concert therewith. Various elements for generating force to the swivable locking member 44, so as to urge movement thereof, may be utilized with the subject invention. In a preferred embodiment, the swivable locking member 44 is fixed to a base 46 via a hinge connection 48. The hinge connection 48 is resiliently distortable so as to permit distortion thereof with inherent resilient biasing force being internally generated urging return of the hinge connection 48 back to the unstressed, natural state shown in FIG. 5.

In a preferred arrangement, the locking tongue 18 is releasably retained in the uncovered position shown in FIG. 4. As will be appreciated by those skilled in the art, any arrangement for releasably retaining the locking tongue 18 consistent with the invention herein may be utilized. In a preferred embodiment, a displaceable locking finger 50 is provided and located to interferingly engage the swivable locking member 44 in an initial, pre-use state (FIG. 4). The displaceable locking finger 50, thus, restricts movement of the swivable locking member 44 under force generated by the biasing element 20, which may be in the form of the hinge connection 48. During use, with the shield 16 being axially displaced relative to the hub 12 from the first shielding position to the second position, described above, the displaceable locking finger 50 is positioned to come into contact with the hub 12 and be displaced upon sufficient contact. In this manner, displaceable locking finger 50 is caused to be displaced and moved out of the interfering position where the displaceable locking finger 50 restricts movement of the swivable locking member 44. As shown in FIG. 5, the locking finger 50 may be displaced below the swivable locking member 44 so that the swivable locking member 44 may be caused to move with the locking tongue 18 to the covering position of FIG. 5 under force of movement by the biasing element 20, which may be in the form of the hinge connection 48.

In a preferred embodiment, the locking tongue 18, the swivable locking member 44, the base 46, the hinge connection 48, and the locking finger 50 are unitarily formed. It is preferred that all these elements be fixed to the shield 16 so as to move therewith. For example, the base 46 may be coupled to the shield 16. More preferably, these elements are unitarily formed from a stamped piece of metal. As shown in FIG. 5, the locking tongue 18 may be formed by a cutting or stamping process which separates the locking tongue 18 from the surrounding portions of the base 46. To ensure sufficient stiffness of the elements, and, thus, dependable operation thereof, the swivable locking member 44 is disposed upwardly relative to the base 46. It is preferred that the hinge connection 48 be located at the end of the swivable locking member 44 further from the locking tongue 18. In addition, it is preferred that free end 52 of the swivable locking member 44 be bent or otherwise reinforced to impart stiffness to the swivable locking member 44.

Figure 6:
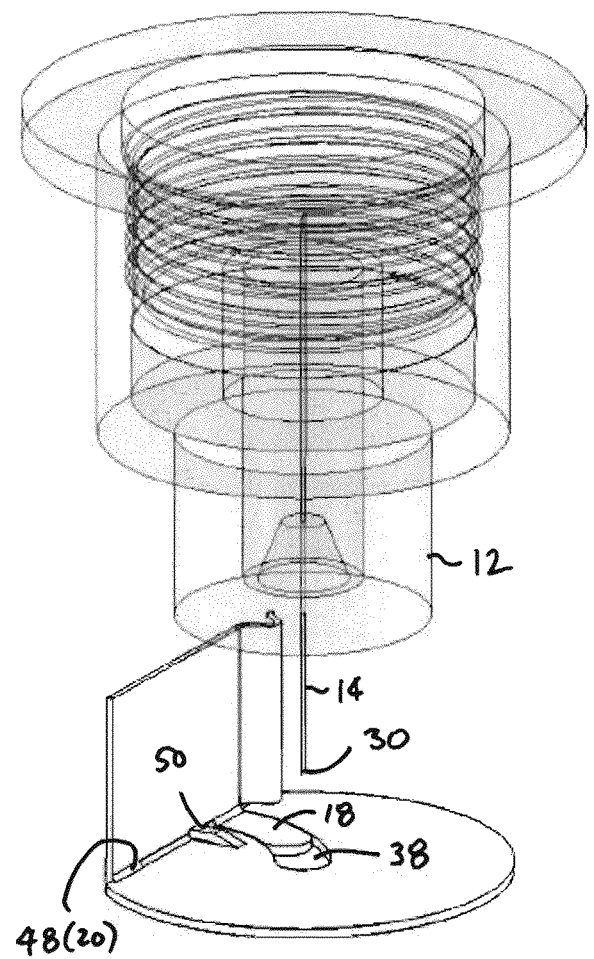
Figure 9:
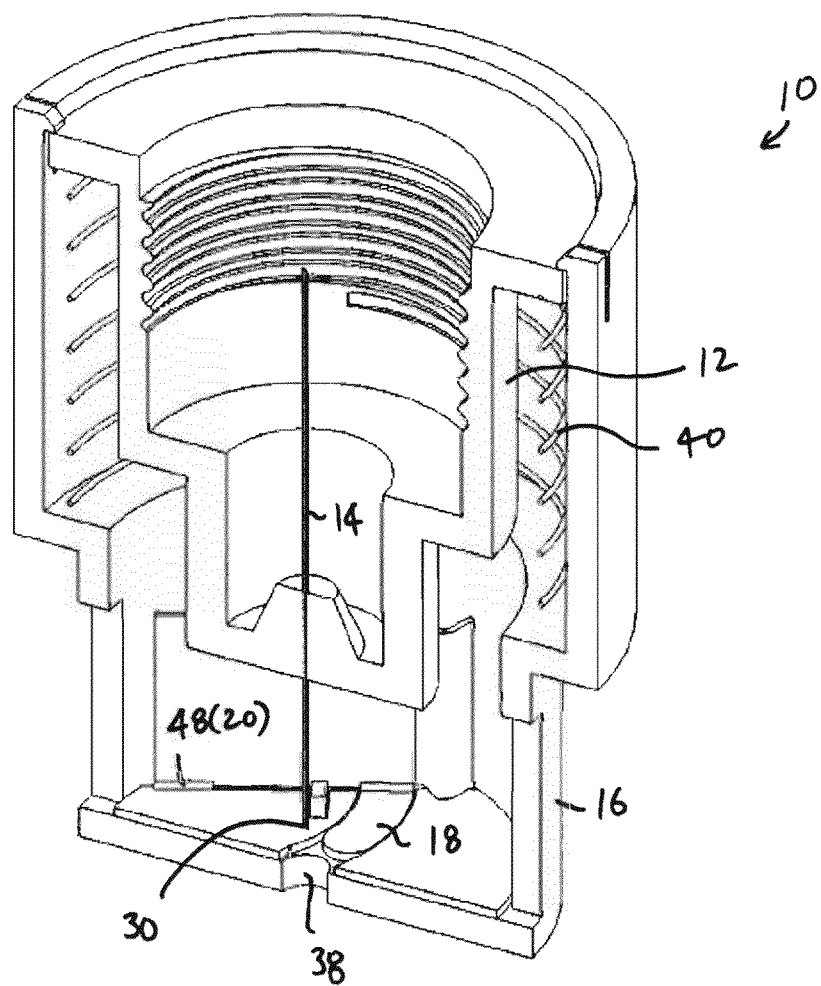
FIGS. 9 and 10 are cross-sectional views of a safety needle assembly formed in accordance with the subject invention showing before and after use states, respectively.

With reference to FIGS. 6 and 9, prior to use, the locking tongue 18 is in the uncovered state, where the distal end 30 of the needle 14 may pass through the aperture 38. The locking tongue 18 is releasably retained by the locking finger 50 in this state. It is noted that the swivable locking member 44 is sufficiently out of alignment with the hub 12 so as to not prevent axially movement thereof during use. In this manner, the hub 12 may move distally to permit injection without engaging the swivable locking member 44.

Figure 7:
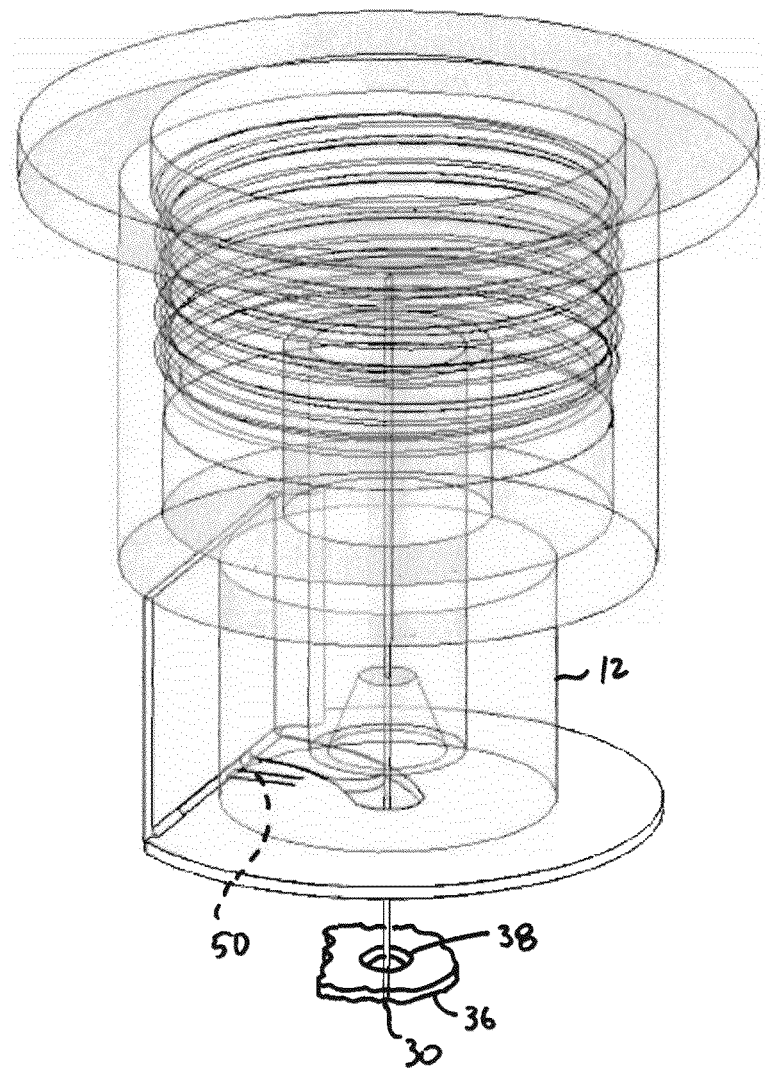

As shown in FIG. 7, during use, the shield 16 is urged proximally from the first position to the second position. With sufficient proximal movement of the shield 16, the needle 14 extends through the aperture 38 with the distal end 30 of the needle 14 being exposed for injection. The hub 12 is configured such that, with sufficient proximal movement of the shield 16 during injection, the hub 12 engages the locking finger 50 so as to cause displacement thereof. It is preferred that the hub 12 and the locking finger 50 be configured and positioned such that the shield 16 may have some proximal movement without the locking finger 50 being engaged. This ensures that a pre-determined amount of proximal movement of the shield 16 is required to engage the locking finger 50, and thus activate the shielding mechanism of the safety needle assembly 10. This also limits the possibility of unintended activation.

Figure 8:
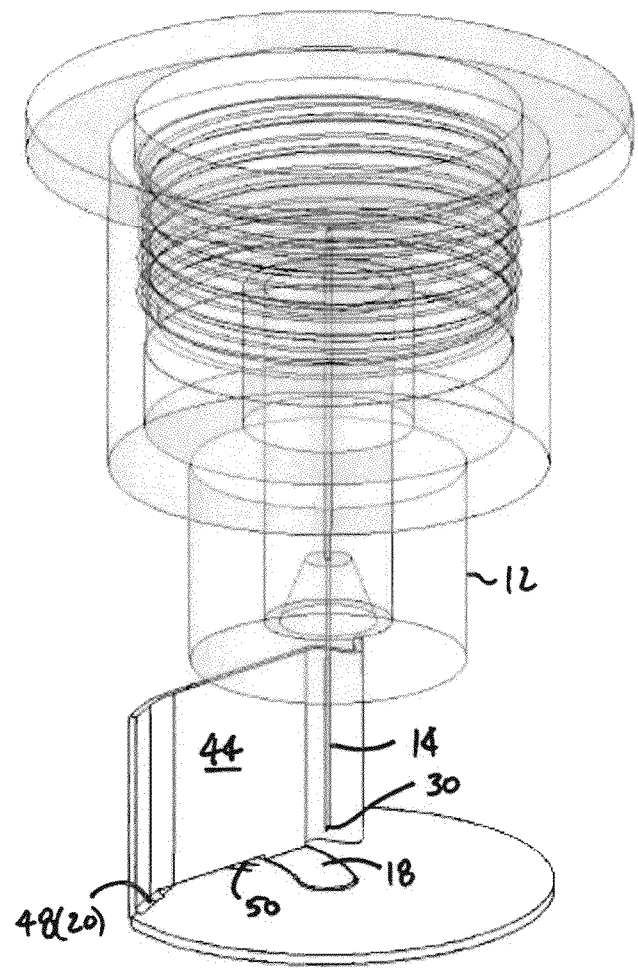
Figure 10:
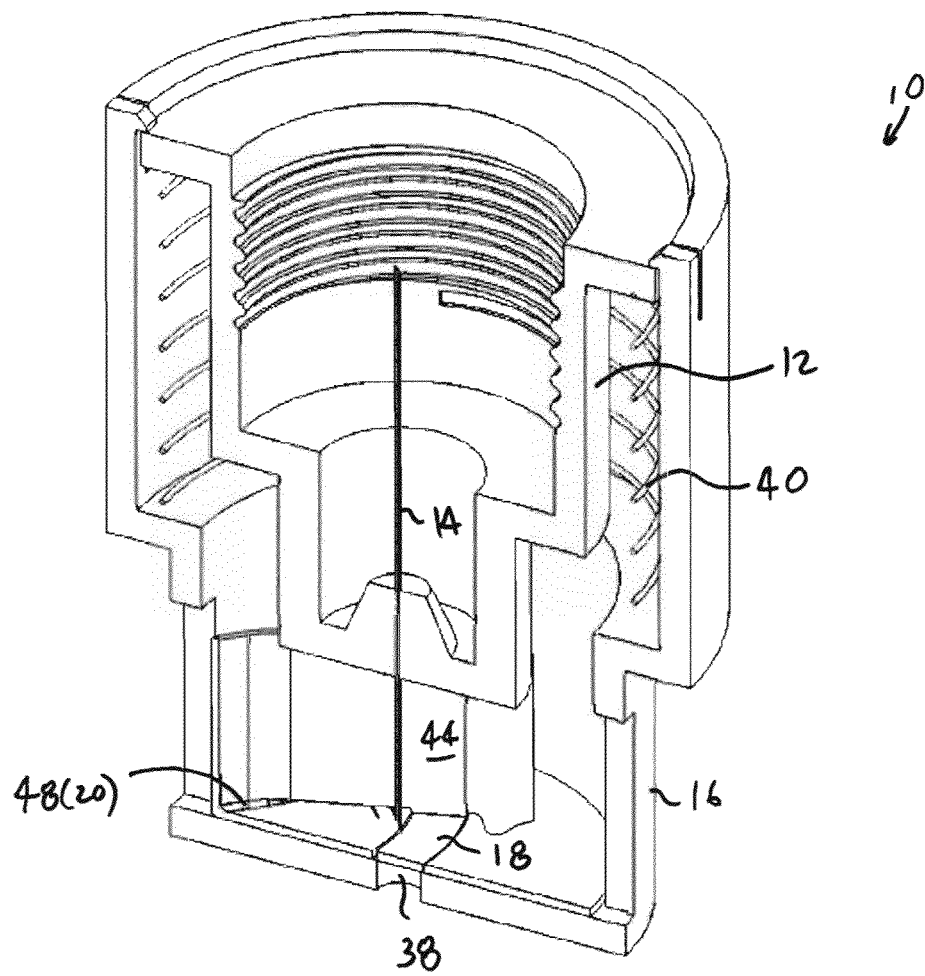

With reference to FIGS. 8 and 10, with the locking finger 50 having been displaced, the swivable locking member 44 is no longer restrained by the locking finger 50. After injection, and with the use of the secondary biasing element 40, the shield 16 is urged to the shielding position with the swivable locking member 44 moving distally relative to the hub 12. With the swivable locking member 44 moving clear of the hub 12, the swivable locking member 44, under force of the biasing element 20, which may be in the form of the hinged connection 48, urges the locking tongue 18 to the covering position shown in FIGS. 8 and 10. It is preferred that the swivable locking member 44 have sufficient height so as to permit movement of the locking tongue 18 once the distal end 30 of the needle 14 is located proximally of the locking tongue 18. The swivable locking member 44 interferingly engages a portion of the hub 12 until the hub 12 is cleared beyond the height of the swivable locking member 44. With this arrangement, the locking tongue 18 is caused to be displaced only once the needle 14 is clear thereof. It is preferred that the locking tongue 18 not strike or engage the needle 14 during an injection or prior to full shielding of the needle 14. With the shielding state as shown in FIG. 10, the locking tongue 18 prevents the needle 14 from entering or passing through the aperture 38.

Figure 11:
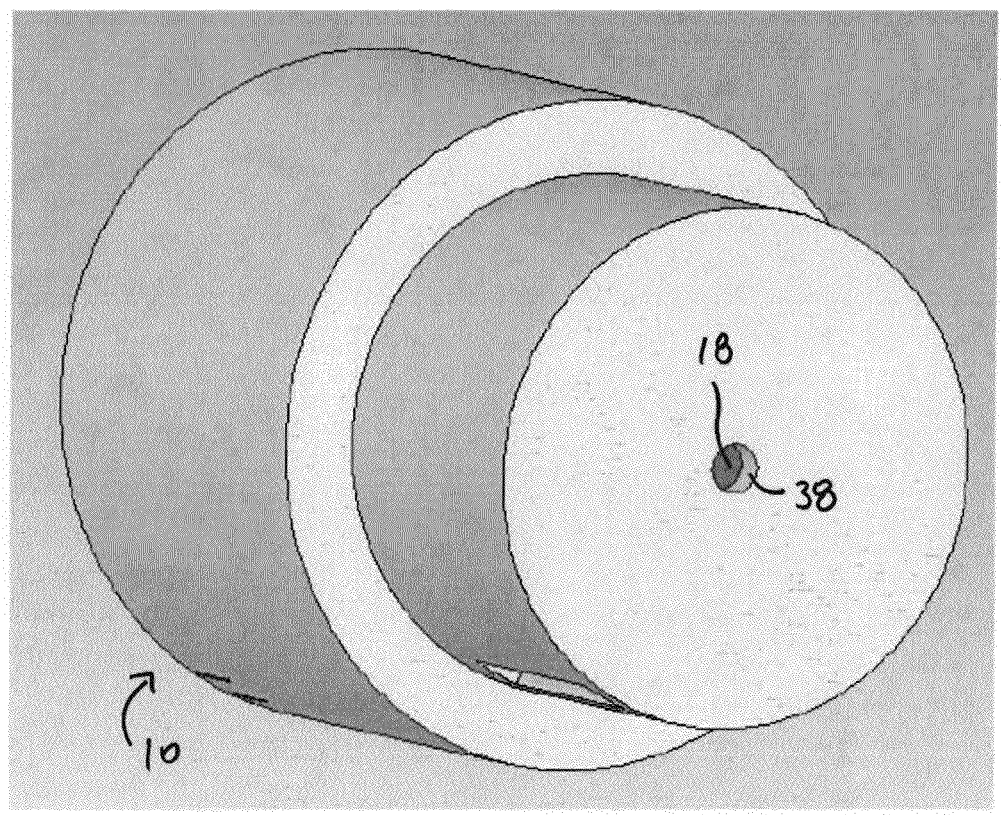
FIG. 11 is an end perspective view of a safety needle assembly formed in accordance with the subject invention after use with the locking tongue acting as a use indicator.
Figure 12:
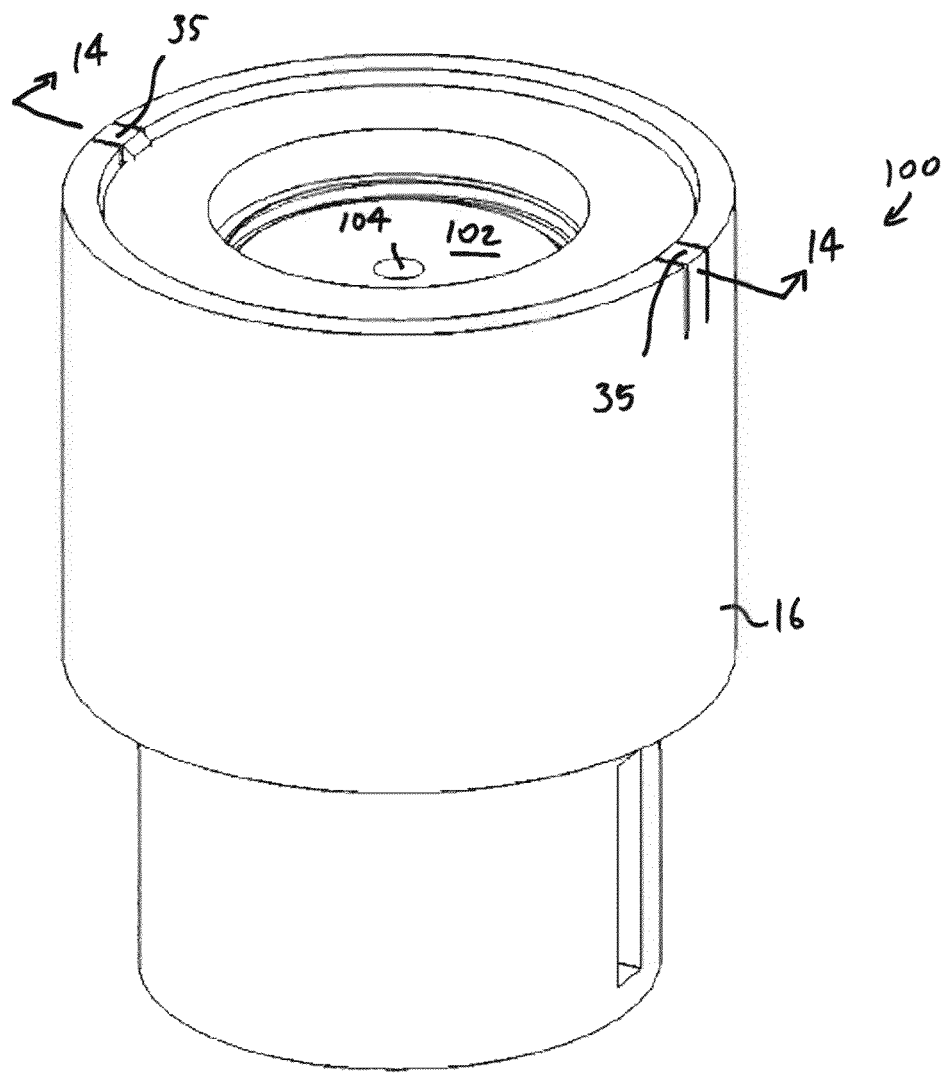
FIG. 12 is a perspective view of a second embodiment of a safety needle assembly formed in accordance with the subject invention.
Figure 13:
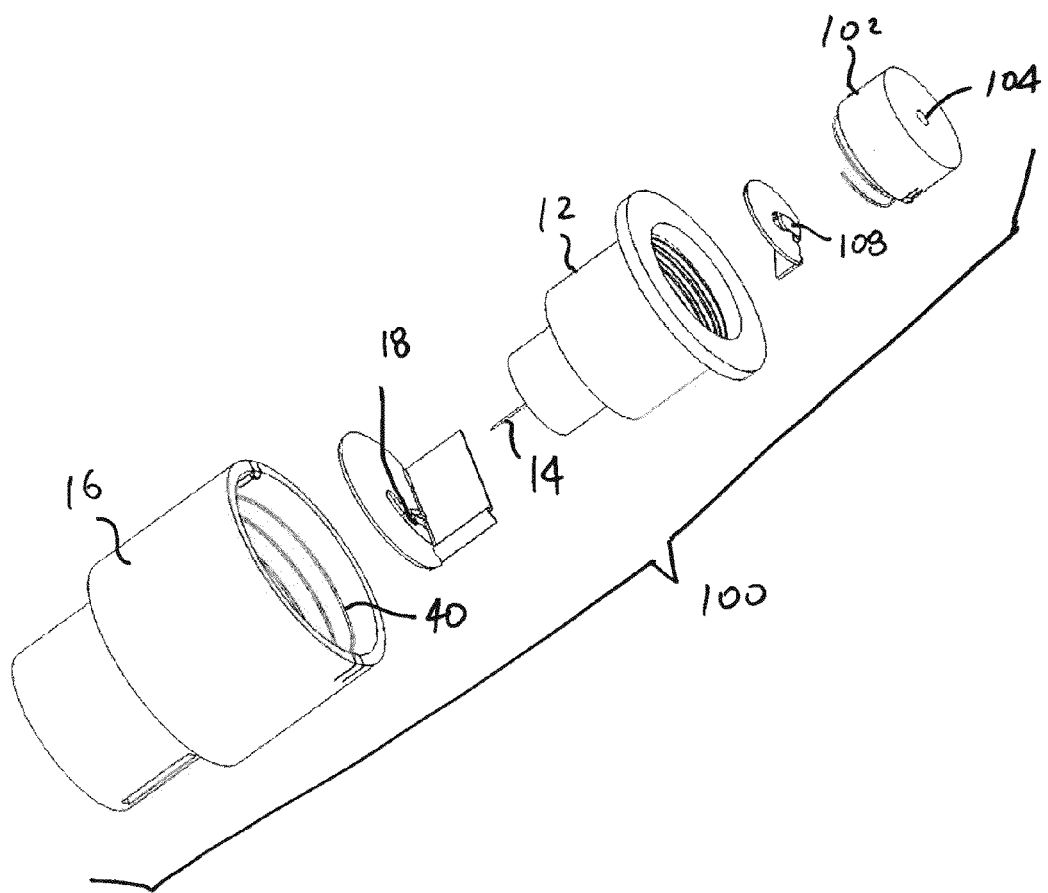
FIG. 13 is an exploded view of a second embodiment of a safety needle assembly formed in accordance with the subject invention.

With reference to FIG. 11, the locking tongue 18 is exposed through the aperture 38 after use. The locking tongue 18, particularly the visible surface thereof, may be formed of a different material and/or color than the shield 16 so as to be readily discerned therefrom. The locking tongue 18, thus, may act as a visual indicator that the safety needle assembly 10 has been used. The locking tongue 18, as will be appreciated by those skilled in the art, may be adorned with various patterns, graphics or other indicia as an additional option or alternatively to that described above.

One or more windows 41 (FIG. 2) may be defined in the shield 16 to permit visual inspection of the needle 14, before, during, or after use.

Figure 14:
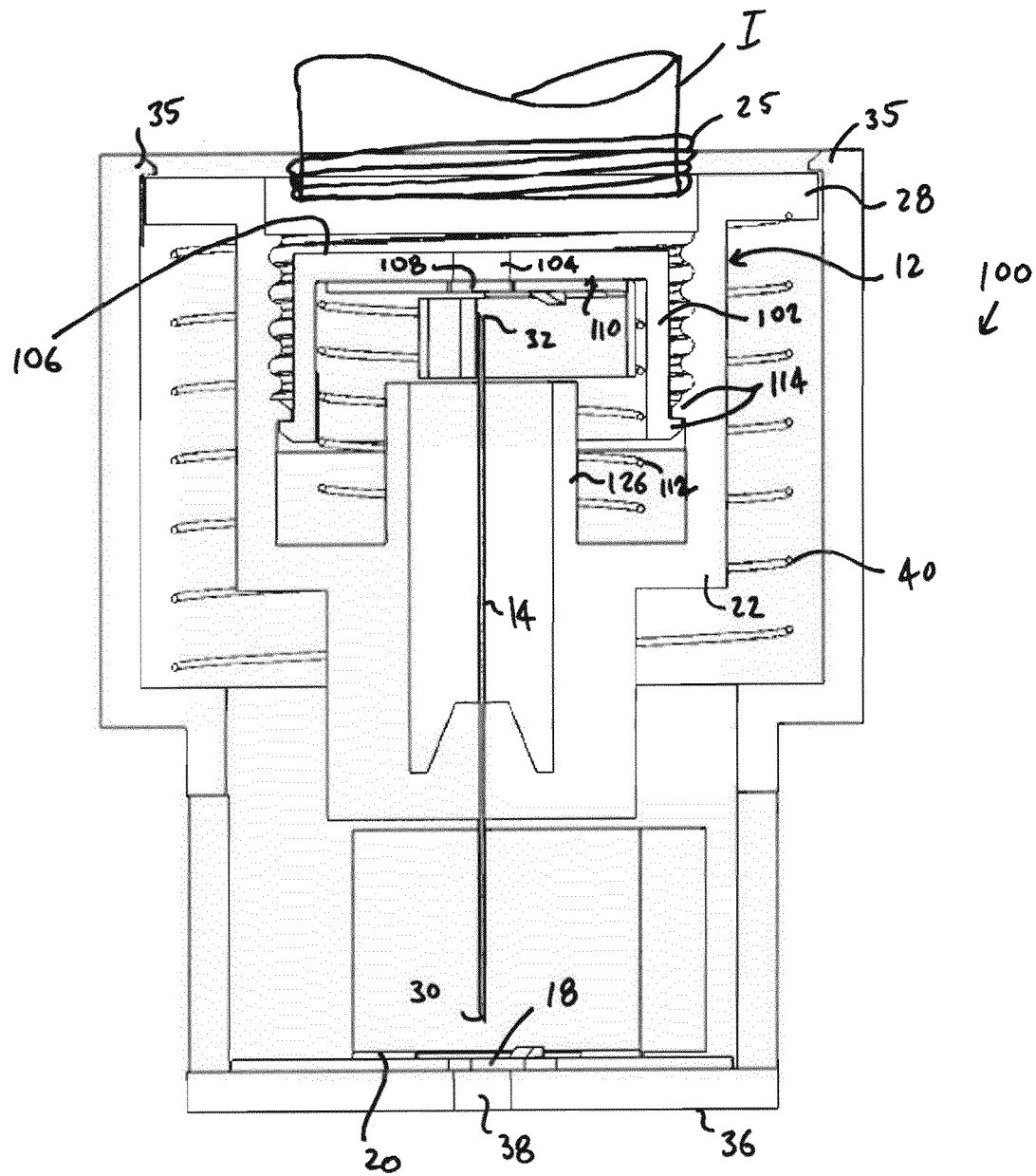
FIG. 14 is a cross-sectional view taken along line 14-14 of FIG. 12.
Figure 25:
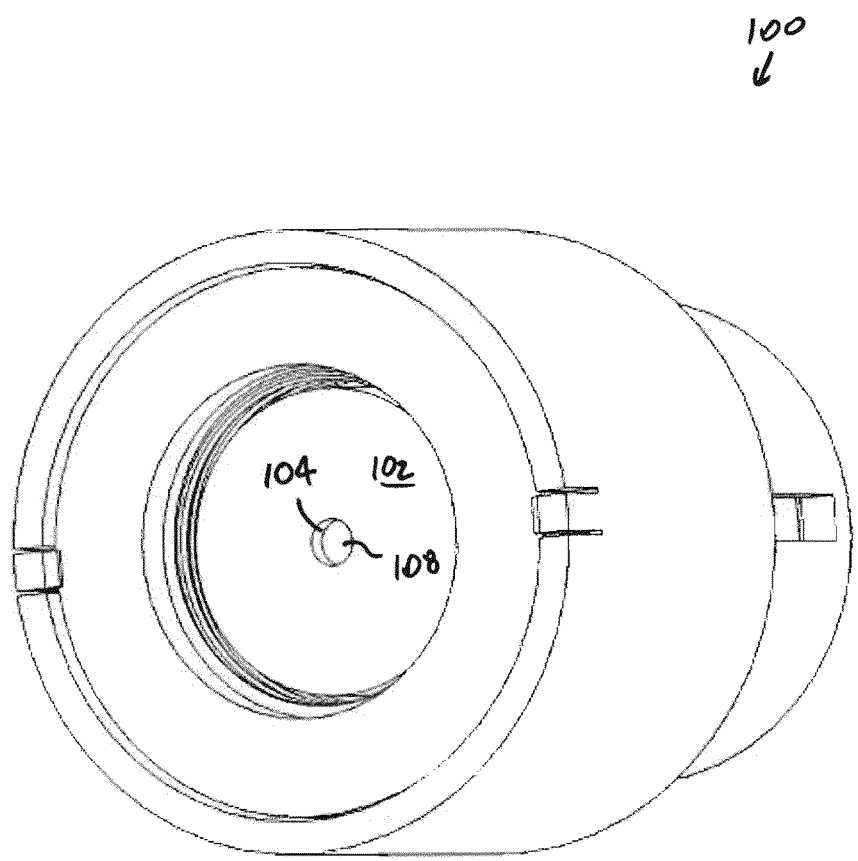
Figure 26:
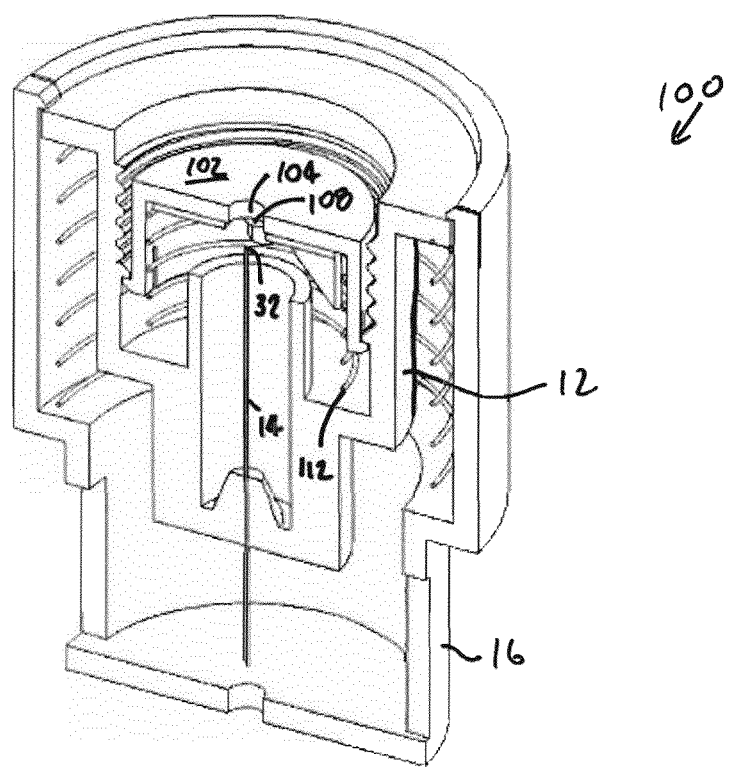
FIG. 26 is a cross-sectional view of a safety needle assembly utilizing only the secondary locking tongue in connection with a proximal end of a needle of a safety needle assembly formed in accordance with the subject invention.

With reference to FIGS. 12-26, with a second embodiment of the invention, a safety needle assembly 100 may be provided which is usable to shield the proximal end 32 of the needle 14. Except as noted below, all discussion from above applies equally hereto. As shown in FIG. 14, both the distal end 30 and the proximal end 32 of the needle 14 may be shielded. Alternatively, as shown in FIG. 26, only the proximal end 32 of the needle 14 may be shielded.

With particular reference to FIGS. 13-21, the safety needle assembly 100 includes a secondary shield 102, having a secondary aperture 104 formed in a proximal end 106 thereof; a secondary locking tongue 108; and, a supporting biasing element 110. The safety needle assembly 100 preferably also includes a secondary supporting biasing element 112 formed to urge the secondary shield 102 in a proximal direction. Cooperating members 114 may be formed on the secondary shield 102 and the hub 12 which limit the proximal movement of the secondary shield 102 under force of the secondary supporting biasing element 112.

The secondary locking tongue 108 operates in the same fashion as the locking tongue 18, except with reference to the secondary aperture 104 formed in the secondary shield 102 so as to provide selective access to the proximal end 32 of the needle 14. The supporting biasing element 110 may be in the form of a hinge connection 116 formed in the same manner as the hinge connection 48. In addition, a secondary swivable locking member 118, a secondary base 120, a secondary displaceable locking finger 122, and a secondary free end 124 may be provided, all formed in the same manner as the corresponding elements described above. These elements, however, may be formed proportionately smaller due to the more restrictive area within the injection receiving portion 22 of the hub 12. The elements are configured to move in concert with the secondary shield 102.

Figure 15:
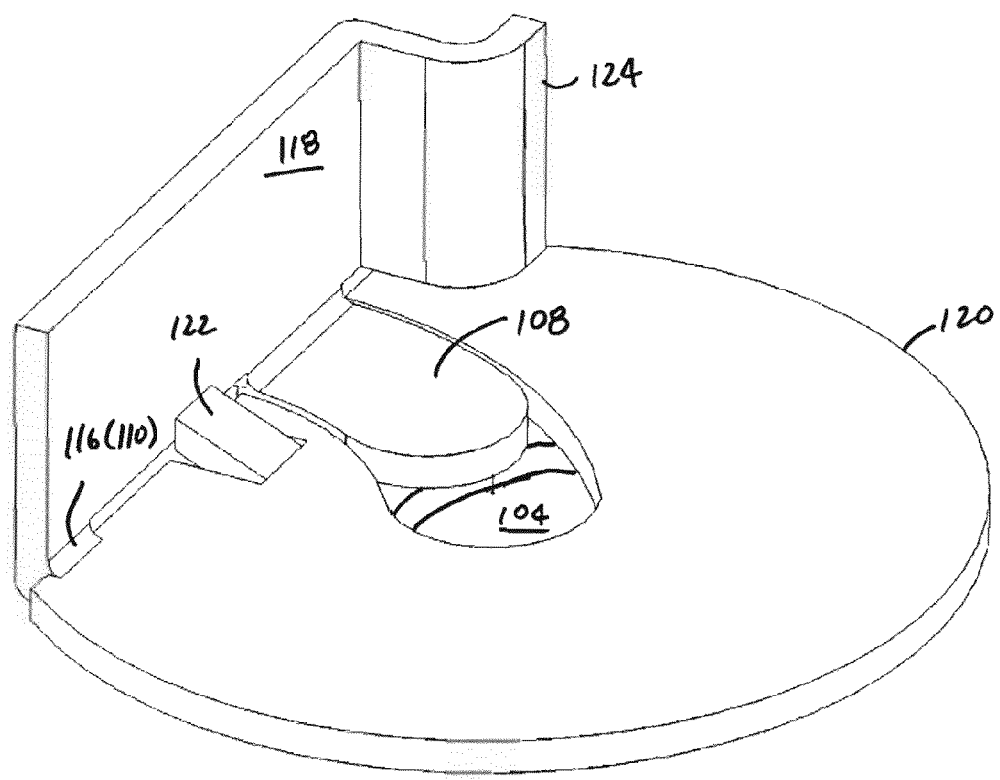
FIG. 15 is a perspective view of a secondary locking tongue formed in accordance with the subject invention being in a retained position.
Figure 16:
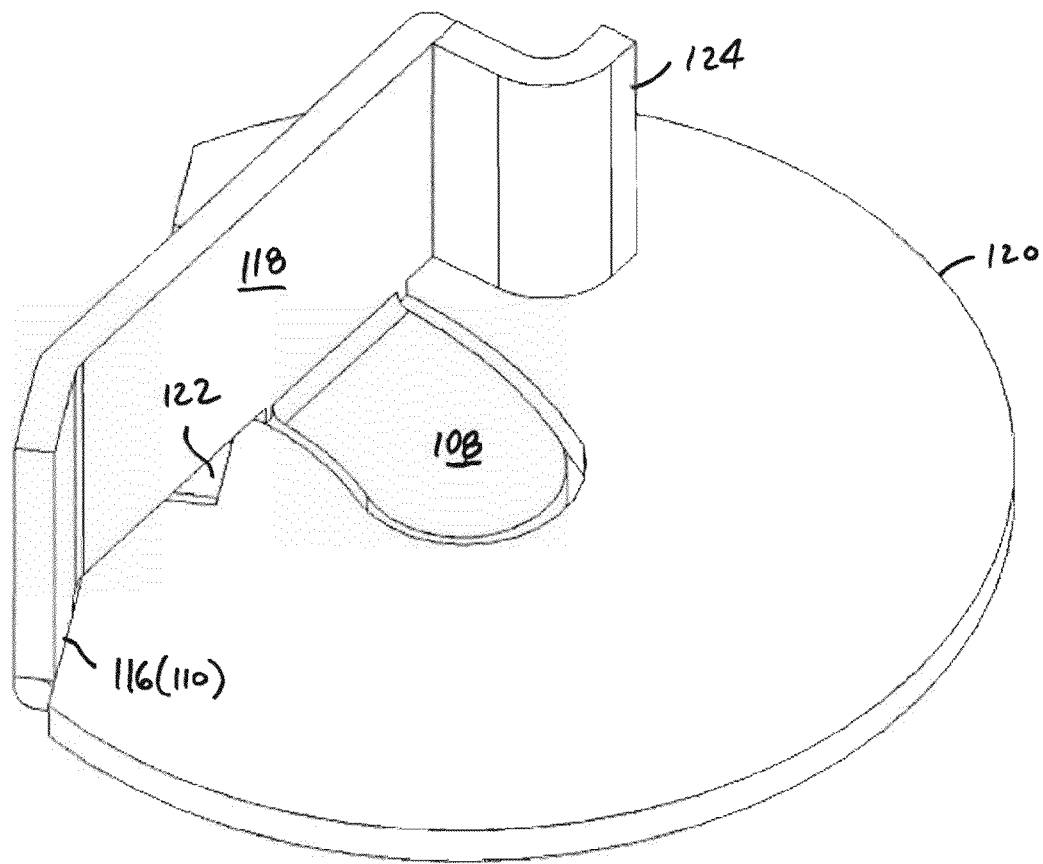
FIG. 16 is a perspective view of a secondary locking tongue formed in accordance with the subject invention being in a covering position.
Figure 17:
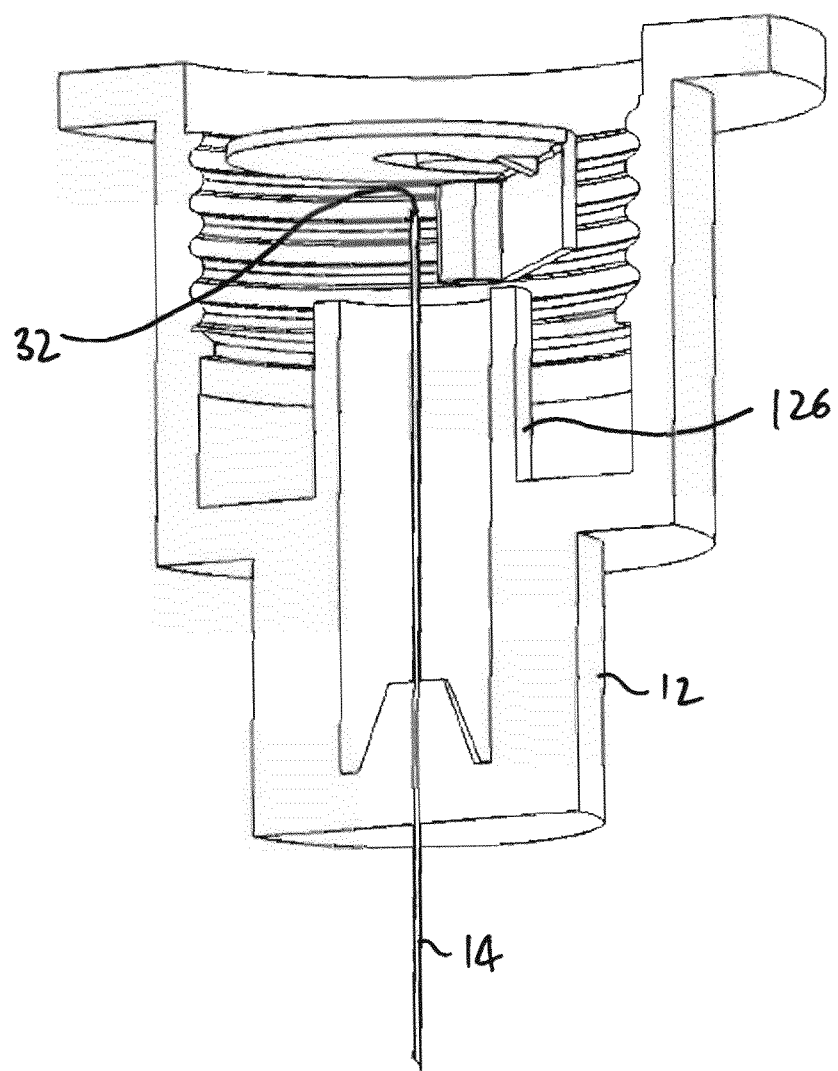
Figure 18:
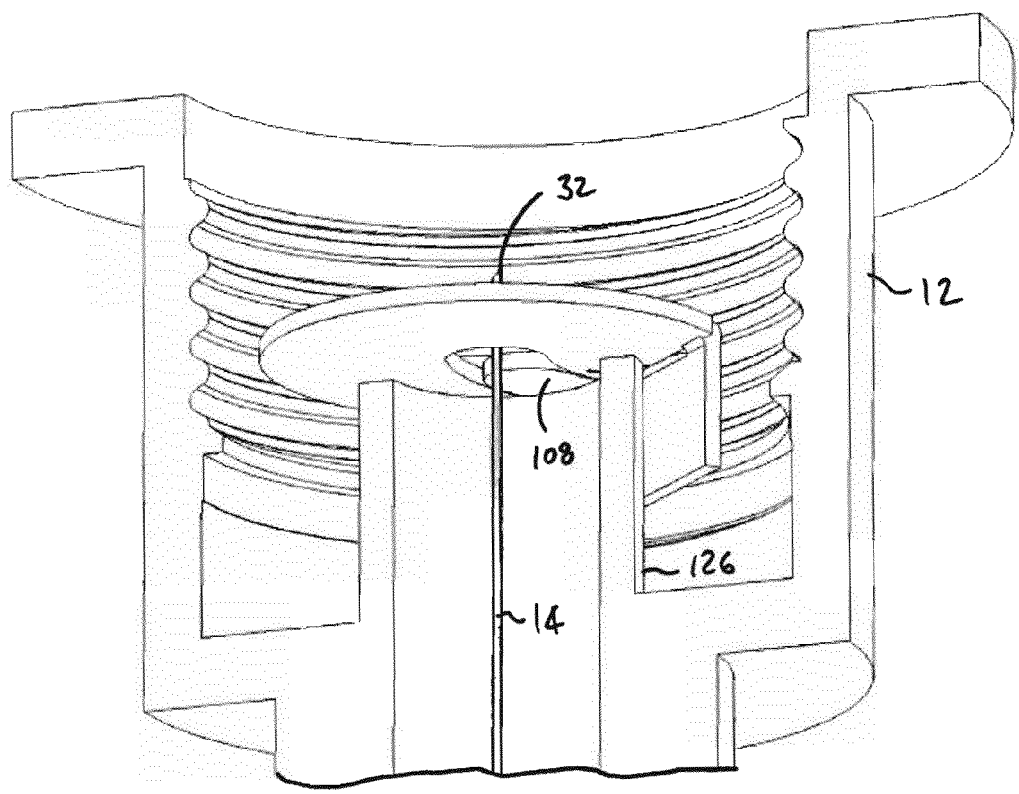
Figure 20:
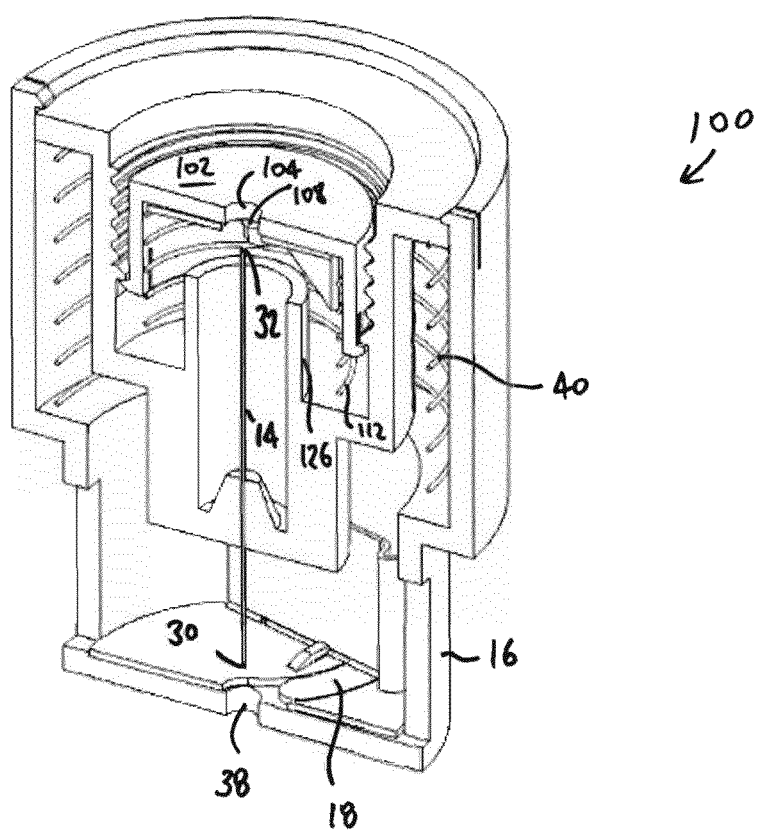
FIGS. 20 and 21 are cross-sectional views of a second embodiment of a safety needle assembly formed in accordance with the subject invention showing before and after use states, respectively.

As shown in FIGS. 15, 17 and 20, preferably, the secondary shield 102 is in an initial position with the proximal end 106 being located proximally of the proximal end 32 of the needle 14. Alternatively, the proximal end 32 of the needle 14 may extend proximally beyond the proximal end 106 in the initial position. Also, the secondary locking tongue 108 is initially in an uncovered position where the proximal end 32 of the needle 14 may pass through the secondary aperture 104. With mounting of the injector I into the injector receiving portion 22, the secondary shield 102 shall be caused to move distally to a second position against force of the secondary supporting biasing element 112. In the second position, the needle 14 extends through the secondary aperture 104 with the distal end 32 being beyond the secondary aperture 104 for use. With sufficient distal movement of the secondary shield 102, a portion of the hub 12 is caused to engage the secondary displaceable locking finger 122 and cause displacement thereof. Preferably, a shaft 126 is provided on the hub 12 positioned and configured to engage the secondary displaceable locking finger 122. In addition, the shaft 126 may interferingly engage the secondary swivable locking member 118 so as to prevent movement of the secondary locking tongue 108 to the covering position prior to the secondary locking tongue 108 being moved clear of the proximal end 32 of the needle 14. In this manner, the secondary locking tongue 108 does not come into contact with the needle 14.

Figure 19:
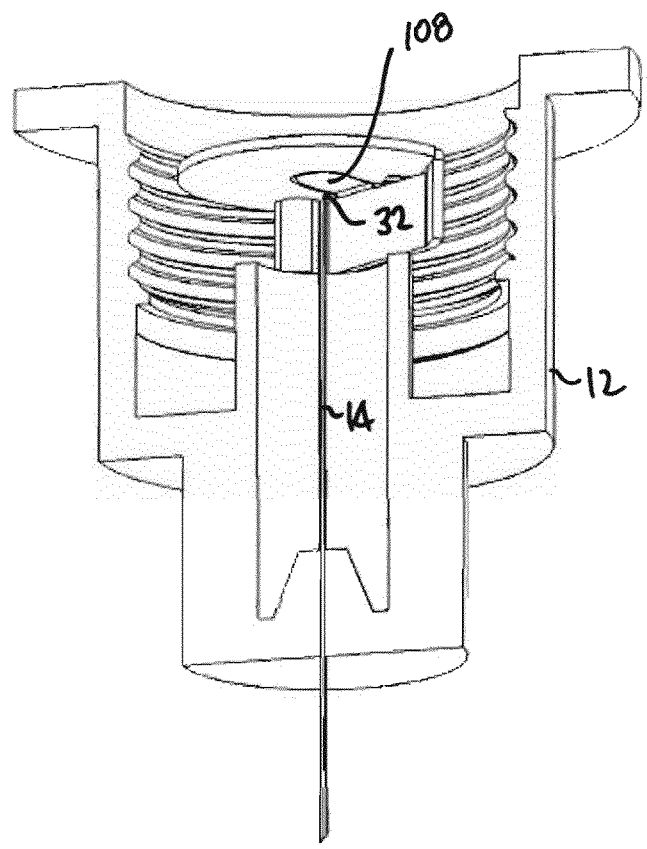
Figure 21:
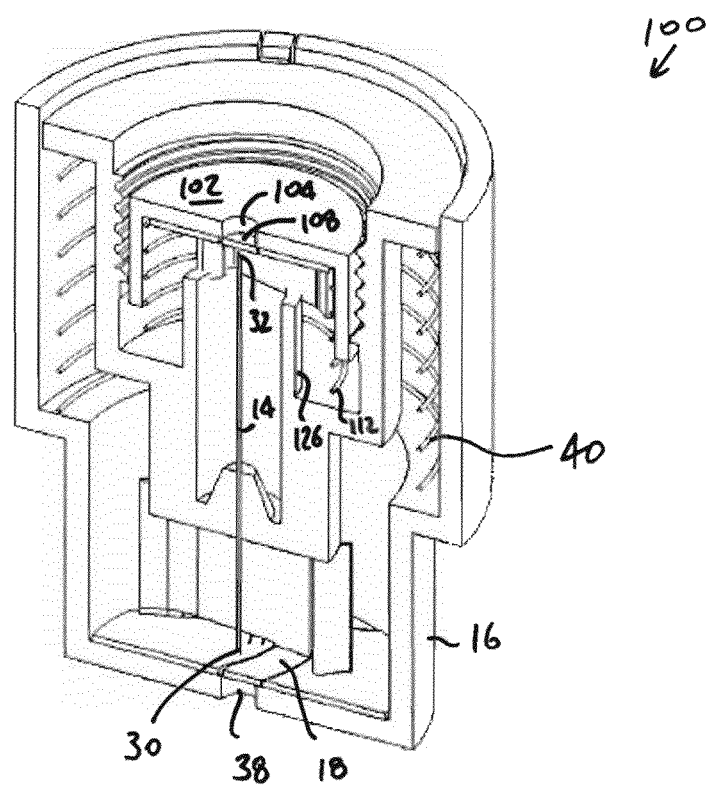
Figure 22:
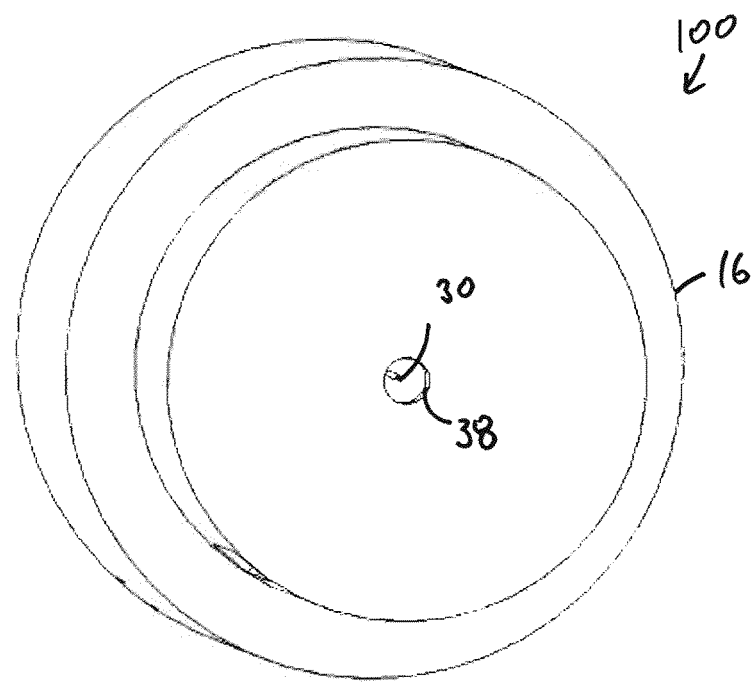
FIGS. 22 and 23 show the distal and proximal ends of a needle, respectively, before use of a second embodiment of a safety needle assembly formed in accordance with the subject invention.
Figure 23:
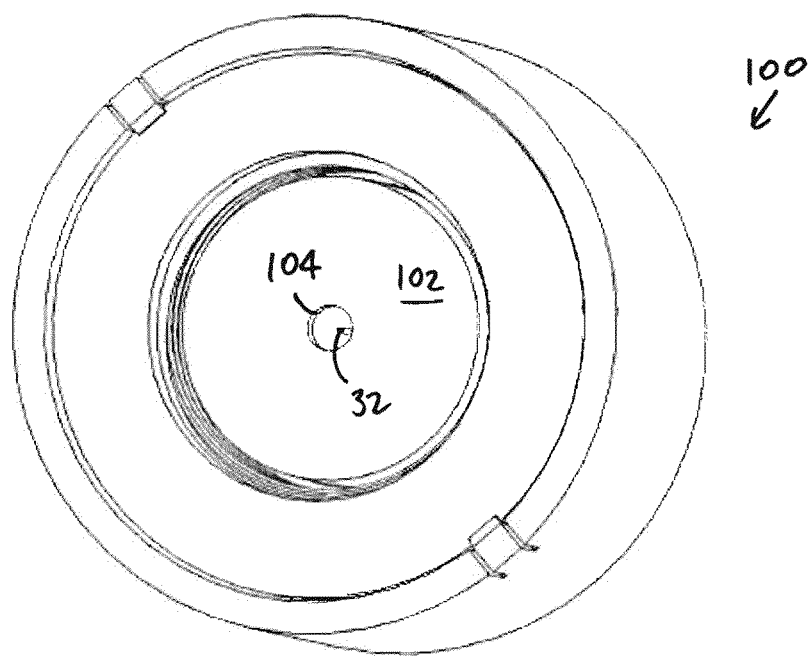
Figure 24:
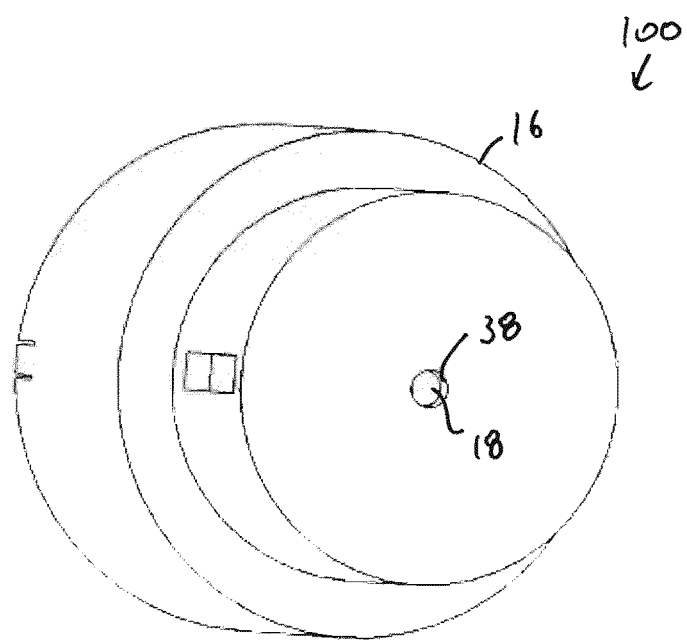
FIGS. 24 and 25 show a locking tongue and a secondary locking tongue, respectively, in covering positions after use of a second embodiment of a safety needle assembly formed in accordance with the subject invention.

FIGS. 19 and 21 show the secondary locking tongue 108 being in the covering position whereby the proximal end 32 of the needle 14 is prevented from accessing the secondary aperture 104. With reference to FIGS. 22 and 23, the distal and proximal ends 30, 32, respectively, of the needle 14 are exposed before use. With reference to FIGS. 24 and 25, with the safety needle assembly 100, both the distal and proximal ends 30, 32 of the needle 14 are both covered by the locking tongue 18 and the secondary locking tongue 108, respectively. As described above with respect to the locking tongue 18, the secondary locking tongue 108 may also be colored or otherwise formed so as to be discernible and act as a use indicator.

With respect to FIG. 26, the safety needle assembly 100 may be provided with only the secondary locking tongue 108 so as to provide shielding only for the proximal end 34 of the needle 14.

What is claimed is:

1. A safety needle assembly comprising:
   a hub;
   a needle fixed to said hub, said needle having a distal end, formed for insertion into a patient, and a proximal end;
   a shield having a tubular body with a proximal end and a distal end, an aperture being formed in said distal end to allow passage therethrough of said distal end of said needle, said shield being axially displaceable proximally relative to said hub from a first position to a second position, said needle extending through said aperture and said distal end of said needle being exposed with said shield being in said second position; and, a displaceable locking tongue, said locking tongue having a first position sufficiently covering said aperture so as to prevent passage therethrough of said distal end of said needle; and, a biasing element for urging said locking tongue to said first position;

wherein, said locking tongue is releasably retained in a retained position prior to use of the safety needle assembly, said aperture being sufficiently uncovered with said locking tongue being in said retained position so as to permit passage of said distal end of said needle through said aperture, said locking tongue being retained in said retained position against biasing force of said biasing element; and, wherein, with said shield being displaced from said first position to said second position, said locking tongue is released from said retained position and urged towards said first position under force of said biasing element, said locking tongue not engaging said needle with said needle extending through said aperture.

2. An assembly as in claim 1 further comprising a secondary biasing element disposed to urge said shield to said first shielding position.

3. An assembly as in claim 1, wherein, said shield is displaced towards said first position after being displaced to said second position.

4. An assembly as in claim 1, wherein said biasing element is a swivable element to which is applied a biasing force urging said swivable element to a rest position, said rest position corresponding to said first position of said locking tongue.

5. An assembly as in claim 4, wherein a displaceable locking finger releasably retains said locking tongue.

6. An assembly as in claim 4, wherein with said shield being displaced from said first position to said second position, said shield displaces said locking tongue so as to release said locking tongue from said retained position.

7. An assembly as in claim 1, wherein said locking tongue includes a surface which is visually discernible from said shield and configured so as to be visible through said aperture and provide an indication of use.

8. An assembly as in claim 1 further comprising a secondary locking tongue for shielding said proximal end of said needle.

9. An assembly as in claim 1, wherein said distal end of said shield is located distally of said distal end of said needle with said shield in said first position.

* * * * *